United States Patent
Wilcke et al.

(10) Patent No.: US 9,687,490 B2
(45) Date of Patent: Jun. 27, 2017

(54) TRIAZINE DERIVATIVES FOR THE TREATMENT OF CONDITIONS ASSOCIATED WITH NICOTINAMIDE ADENINE DINUCLEOTIDE PHOSPHATE OXIDASE

(71) Applicant: GLUCOX BIOTECH AB, Stockholm (SE)

(72) Inventors: Mona Wilcke, Stockholm (SE); Erik Walum, Stockholm (SE); Per Wikstrom, Farentuna (SE)

(73) Assignee: GLUCOX BIOTECH AB, Stockholm (SE)

( * ) Notice: Subject to any disclaimer, the term of this patent is extended or adjusted under 35 U.S.C. 154(b) by 0 days.

(21) Appl. No.: 14/437,678

(22) PCT Filed: Oct. 22, 2013

(86) PCT No.: PCT/EP2013/072098
§ 371 (c)(1),
(2) Date: Apr. 22, 2015

(87) PCT Pub. No.: WO2014/064118
PCT Pub. Date: May 1, 2014

(65) Prior Publication Data
US 2015/0283146 A1 Oct. 8, 2015

Related U.S. Application Data

(60) Provisional application No. 61/717,803, filed on Oct. 24, 2012.

(30) Foreign Application Priority Data

Oct. 24, 2012 (EP) ..................................... 12189823

(51) Int. Cl.
*A61K 31/53* (2006.01)
*A61K 31/4196* (2006.01)
*C07D 251/00* (2006.01)
*C07D 251/18* (2006.01)

(52) U.S. Cl.
CPC .......... *A61K 31/53* (2013.01); *A61K 31/4196* (2013.01); *C07D 251/00* (2013.01); *C07D 251/18* (2013.01)

(58) Field of Classification Search
CPC .. A61K 31/53; A61K 31/4196; C07D 251/00; C07D 251/18
See application file for complete search history.

(56) References Cited

U.S. PATENT DOCUMENTS

2009/0163545 A1* 6/2009 Goldfarb .............. A61K 31/122
514/312

FOREIGN PATENT DOCUMENTS

| WO | 2010/035217 A1 | 4/2010 |
|----|----------------|--------|
| WO | 2010/035219 A2 | 4/2010 |
| WO | 2010/035220 A1 | 4/2010 |
| WO | 2010/035221 A1 | 4/2010 |
| WO | 2011/036651 A1 | 3/2011 |
| WO | 2011/101804 A1 | 8/2011 |
| WO | 2011/101805 A1 | 8/2011 |

OTHER PUBLICATIONS

Database PubChem Compound [Online] Jul. 10, 2005 (Jul. 10, 2005), "ACIL0516—Compound Summary", XP002690384, retrieved from NCBI Database accession No. 1214343 (CID) the whole document.
Database PubChem Compound [Online] Jul. 10, 2005 (Jul. 10, 2005), "ACIL0519—Compound Summary", XP002690385, retrieved from NCBI Database accession No. 1214344 (CID) the whole document.
Database PubChem Compound [Online] Jul. 10, 2005 (Jul. 10, 2005), "N-(3,4-dimethylphenyl)-6-{[4-(3-methoxyphenyl) piperazin-l-yl]methyl}-1,3,5-triazine-2,4-diamine—Compound Summary", XP002690386, retrieved from NCB1 Database accession No. 1214345 (C1D) the whole document.
Database PubChem Compound [Online] Jul. 10, 2005 (Jul. 10, 2005), "STK567131—Compound Summary", XP002690387, retrieved from NCB1 Database accession No. 1214348 (C1D) the whole document.
International Search Report, dated Dec. 12, 2013, from corresponding PCT application.

* cited by examiner

*Primary Examiner* — Sahar Javanmard
(74) *Attorney, Agent, or Firm* — Young & Thompson

(57) ABSTRACT

A compound of formula (I) for use in the treatment of a condition or disorder associated with nicotinamide adenine dinucleotide phosphate oxidase.

23 Claims, 2 Drawing Sheets

TRIAZINE DERIVATIVES FOR THE TREATMENT OF CONDITIONS ASSOCIATED WITH NICOTINAMIDE ADENINE DINUCLEOTIDE PHOSPHATE OXIDASE

FIELD OF THE INVENTION

The present invention relates to triazine derivatives for use in the treatment of a condition or disorder associated with nicotinamide adenine dinucleotide phosphate oxidase (Nox). More specifically, the present invention relates to triazine derivatives as Nox inhibitors for use in the treatment of various diseases that are caused or driven by elevated Nox activity. In particular the invention relates to compounds having selectivity for Nox4.

BACKGROUND OF THE INVENTION

The definition of oxidative stress is an in vivo imbalance between the formation and elimination of reactive oxygen. Changes of the normal redox state in the cell or tissues can produce harmful radicals that may damage components of the cellular machinery, including DNA, proteins and lipids. If the cellular components are chemically altered that cause genetic changes, this has generally been considered to promote formation of cancer or other serious diseases.

Sources of Oxygen Radicals—

Numerous in vivo generators of oxygen radicals ($O_2^-$, $H_2O_2$ and $OH^-$) that potentially can cause oxidative stress have been identified: complex I and III in the mitochondria and NAD(P)H oxidase, xanthine oxidase, cytochromes P450, metal ions (cobalt, vanadium, chromium, copper and iron) and some organic compounds that can redox cycle.

General Antioxidants—

There also are numerous endogenously cellular antioxidants such as superoxide dismutase (SOD), catalase, glutathione peroxidase, peroxiredoxins and sulfiredoxin. Vitamins provided by the food are also considered as an important part of the protection of the organism from harmful oxygen radicals, and recent discovery of important antioxidants present in many sources of food has increased the arsenal of antioxidants.

Antioxidants as Therapeutics—

It is very clear that some antioxidants can be helpful in preventing diseases and promote health. What is much less clear is what type of antioxidants can be used. Many of the antioxidants present in natural food are redox active. If these types of redox active substances are isolated and provided as complementary pharmaceuticals—this may end up being more harmful than helpful. Clinical trials have shown that untargeted application of antioxidants, which broadly scavenge oxygen radicals, are not only ineffective but may even be harmful. This was illustrated in a study made with sixty-seven randomized trials with 232,550 participants including healthy and patients with various diseases (Bjelakovic G, Nikolova D, Simonetti R G, Gluud C. Cochrane Database Syst Rev. 2008 Jul. 16; (3):CD004183. Epub 2008 Jul. 16).

Thus general antioxidants that are redox active may actually be adding to the cellular damage, by mediating a harmful redox cycle. Other general antioxidants will harmfully block normal cellular in vivo activity necessary to maintain bodily function.

Source and Role of Reactive Oxygen—

What has become increasingly clear is that what is causing excessive production and accumulation of reactive oxygen, in a number of pathological conditions, such as inflammation, type 2 diabetes, diabetes complications, polycystic ovary syndrome, stroke, detrimental neurological conditions and cancer, is not generally leaking oxygen radicals such as complex I or III in the mitochondria—rather it is up-regulated powerful producers of oxygen radicals—that are part of the normal cellular signal transduction system. Thus the definition of oxidative stress need not be oxygen radicals that will irreversibly alter DNA, protein or lipids, but instead increasingly interfere, if up regulated with "normal" signal transduction creating an imbalance on a cellular level that eventually may alter other tissues and whole bodily function. A typical example of this is the metabolic syndrome, connected to vascular disease, diabetes 2, stroke, nephropathy, neuropathy, heart failure and stroke with insulin resistance as the initiating factor (Reaven, "Role of insulin resistance in human disease", Diabetes 37(12), 1988). Insulin resistance in itself is also part of normal bodily function as a tool to direct storage of energy selectively to a suitable receiving organ. However, when metabolic changes occur, such as in overfeeding, or other disturbances such as acromegaly with excess growth hormone production or malfunctioning leptin as in ob/ob-mice, this will induce a harmful condition with an uncontrolled insulin resistance that may cause organ failure connected to the metabolic syndrome. The common denominator to the uncontrolled insulin resistance is overproduction of local and systemic oxygen radicals (Houstis et al., Nature 440, 2006; Katakam et al., J cereb blood Flow Metab, 2012 Jan. 11).

One of the most interesting candidates for this overproduction is a family of trans-membrane proteins (enzymes), referred to as NAD(P)H oxidase (Nox). There are seven family members of Nox identified (Nox 1-5 and Duox 1-2) that very often are being recognized as a major or key source of reactive oxygen and that also play a major role in a number of cellular events as part of the normal cellular signal transduction system, including proliferation (Brar et al., Am J Physiol Lung Cell Mol Physiol, 282, 2002), growth (Brar et al., Am J Physiol Cell Physiol, 282, 2002), fibrosis (Grewal et al., Am J Physiol, 276, 1999), migration (Sundaresan et al., Science, 270, 1995), apoptosis (Lundqvist-Gustafsson et al., J Leukoc Biol, 65, 1999), differentiation (Steinbeck et al., J Cell Physiol, 176, 1998), cytoskeletal rearrangement (Wu et al., J Virol, 78, 2004) and contraction (Rueckschloss et al., Exp Gerontol, 45, 2010).

NADPH Oxidase and Disease—

Some genetic conditions with decreased NADPH oxidase activity have been identified—defect Nox2 decreases immunologic response to kill and neutralize microbial attacks (Chronic granulomatous disease)—defect Nox3 in inner ear renders defective gravity perception and dual NAD(P)H oxidase Duox2 having deficient enzymatic activity in the thyroid gland gives rise to hypothyroidism.

There is however a much larger list of publications that also seems to grow exponentially, that witness of strong evidence that increased Nox activity is part of or even causative of a number of diseases (Lambeth J D, Review Article "*Nox enzymes, ROS, and chronic disease: An example of antagonistic pleiotropy*", Free Radical Biology & Medicine 43, 2007; Takac I et al., "*The Nox Family of NADPH Oxidases: Friend or Foe of the Vascular System*", Curr Hypertens Rep. 2011 Nov. 10; Montezano A C, "*Novel Nox homologues in the vasculature: focusing on Nox4 and Nox5*", Clin Sci London 2011; Bedard K et al., "*The Nox family of ROS-generating NADPH oxidases: physiology and pathophysiology*" Physiol Rev. 2007; Camici M et al., "Obesity-related glomerulopathy and podocyte injury: a mini review", Front Biosci 2012; Nabeebaccus A et al., "NADPH oxidases and cardiac remodeling" Heart Fai Rev. 2011; Kuroda J et al., "NADPH oxidase and cardiac failure" J Cardiovasc Transl Res. 2010; Kuroda J et al., "NADPH oxidase 4 is a major source of oxidative stress in the failing heart" Proc Natl Acad Sci USA 2010; Maejima Y et al., "Regulation of myocardial growth and death by NADPH oxidase" J Mol Cell Cardiol. 2011; Barnes J L et al., "Myofibroblst differentiation during fibrosis: role of NAD (P)H oxidases" Kidney international, 2011; Alison Cave "Selective targeting of NADPH oxidase for cardiovascular protection" Current Opinion in Pharmacology 2009; Albert van der Vliet "Nox enzymes in allergic airway inflammation" Biochimica et Biophysica Acta 1810, 2011; Pendyala S et al., "Redox regulation of Nox proteins" Respiratory Physiology & Neurobiology 174, 2010; Nair D et al., "Intermittent Hypoxia-Induced Cognitive Deficits Are Mediated by NADPH oxidase Activity in a Murine Model of Sleep Apnea" PLoS ONE, vol. 6, Issue 5, May 2011; Chia-Hung Hsieh et al., "NADPH oxidase Subunit 4-Mediated Reactive Oxygen species Contribute to Cycling Hypoxia-Promoted Tumor Progression in Glioblastoma Multiforme" PloS ONE, vol 6, issue 9, September 2011; Sedeek M et al., "Molecular mechanisms of hypertension: role of nox family NADPH oxidase" Current Opinion in Nephrology and Hypertension 2009; Augusto C et al., "Novel Nox homologues in the vasculature: focusing on Nox4 and Nox5" Clinical Science 2011; Briones A M et al., "Differential regulation of Nox1, Nox2 and Nox4 in vascular smooth muscle cells from WKY and SHR" Journal of the American Society of Hypertension 5:3, 2011).

It has been recently shown that the Nox enzymes and particularly Nox 4 and NAD(P)H-oxidase are highly involved in pulmonary fibrosis. The function of oxidative stress in fibrosis are well recognized (Kinnula V L, Fattman C L, Tan R J, Oury T D (2005) Oxidative stress in pulmonary fibrosis: a possible role for redox modulatory therapy. Am J Respir Crit Care Med 172:417-422), as there is a substantial and growing body of evidence indicating that oxidative stress plays an important role in the pathological development of lung fibrosis as well as fibrosis in multiple organ systems (Kuwano K, Nakashima N, Inoshima I, Hagimoto N, Fujita M, Yoshimi M, Maeyama T, Hamada N, Watanabe K, Hara N (2003) Oxidative stress in lung epithelial cells from patients with idiopathic interstitial pneumonias. Eur Respir J 21:232-240). Thus, Nox enzymes and particularly Nox4 appear to be involved also in lung infections, acute lung injury, pulmonary arterial hypertension, obstructive lung disorders, fibrotic lung disease, and lung cancer.

NADPH Oxidase Isoenzymes, Similarities, Differences and Function—

All the seven isoenzymes of NADPH oxidase (identified) are similar in the way of having NADPH and FAD binding site and six trans-membrane domains and in that they include two heme complexes. All the NADPH oxidase forms use the same basic mechanism to generate reactive oxygen, but the subcellular localizations and the modes of actions differ significantly. The reactive oxygen species produced by the enzymatic Nox-family are either superoxide $O_2^-$ or hydrogen peroxide $H_2O_2$.

Nox1 and 2 are constitutively attached to p22phox and to activate the enzyme complex other components such as Rac, p47phox, p67phox are required for full Nox1 activity. Nox2 needs Rac, p40phox, p47phox and p67phox for full activation. Nox1 and 2 generate $O_2^-$ when activated.

Nox3 also needs to assemble cytosolic proteins to be active (Cheng et al., J Biol Chem, 279(33), 2004).

Nox4 is also associated with p22phox, and is constitutively active in this form. Nox4 activity is, however, regulated through expression—not through assembly or ligand activation, which distinguishes this isoform from other isoforms (Serrander et al., Biochem J. 406, 2007). When induced, Nox4 is generally expressed at higher level than Nox1 and 2 (Ago et al., Circulation, 109, 2004). Nox4 seems to mainly generate $H_2O_2$ instead of $O_2^-$ as the other Nox-variants (Takac et al., J. Biol. Chem. 286, 2011). This makes this isoform unique because $H_2O_2$ has the ability to cross membranes and thus to act at longer distance than $O_2^-$ that has a very short half-life.

Nox5, Doux1 and Doux2 are activated by $Ca^{21}$ (De Deken, Wang et al., J. Biol Chem., 275(30), 2000).

Nox4 and Diseases—

The uniqueness of Nox4 in comparison to the other isoforms is also connected to uniqueness as a therapeutic target as it seems to be involved in a number of different diseases when overexpressed.

Nox4 is ubiquitously expressed in many cell-types although at a very low level until induced. It is, however, mainly found in kidney, endothelial cells, adventitial fibroblasts, placenta, smooth muscle cells, osteoclasts and is the predominant Nox that is expressed in tumors (Chamseddine et al., Am J Physiol Heart Circ Physiol. 285, 2003; Ellmark et al., Cardiovasc Res. 65, 2005; Van Buul et al., Antioxid Redox Signal. 7, 2005; Kawahara et al., BMC Evol Biol. 7, 2007; Krause et al., Jpn J Infect is. 57(5), 2004; Griendling, Antioxid Redox Signal. 8(9), 2006). It was found that Nox4 was overexpressed in the majority of breast cancer cell-lines and primary breast tumors. Overexpression of Nox4 in already transformed breast tumor cells showed increased tumorigenicity, and Nox4 was here identified in the mitochondria. Nox4 was suggested as a target to treat breast cancer (Graham et al., Cancer Biol Ther 10(3), 2010).

Nox4 mediates oxidative stress and apoptosis caused by TNF-α in cerebral vascular endothelial cells (Basuroy et al., Am J Physiol Cell Physiol vol. 296, 2009). Its adverse effect following ischemic stroke is well demonstrated in animal models and human tissue. Knockdown experiment, of Nox4, dramatically reduced the area of neuronal damage (Sedwick, PLos Biology, vol. 8 issue 9, 2010; Kleinschnitz et al., vol. 8 issue 9, 2010)

It was demonstrated through knockdown and overexpression studies in both microvascular and umbilical vein endothelial cells that increased Nox4 activity plays an important role in proliferation and migration of endothelial cells (Datla et al., Arterioscler Throm Vasc Biol. 27(11), 2007). Initially it was believed that Nox2 was responsible for the angiogenic defects in diabetes but the focus has shifted more towards Nox4 (Zhang et al., PNAS, 107, 2010; Garriodo-Urbani et al., Plos One 2011; Takac et al., Curr Hypertens Rep, 14, 2012). Nox4 play a key role in epithelial cell death during development of lung fibrosis (Camesecchi et al., Antiox Redox Signal. 1:15(3), 2011).

It further was demonstrated that siRNA-mediated knockdown of Nox4 significantly reduces NADPH oxidase activity in purified mitochondria from mesangial cells and kidney cortex. The knockdown blocked glucose-induced mitochondrial superoxide generation. It was suggested that Nox4 acts as a central mediator to oxidative stress that may lead to mitochondrial dysfunction and cell injury in diabetes (Block et al., PNAS vol. 106, no. 34, 2009).

It also was demonstrated that Nox4 was systemically up-regulated at diet-induced obesity in rats (Jiang, redox rep, 16(6), 2011).

Nox4 has been strongly connected to the pathology in failing hearts. (Nabeebaccus A et al. "NADPH oxidases and cardiac remodeling" Heart Fai Rev. 2011; Kuroda J et al., "NADPH oxidase and cardiac failure Cardiovasc Transl Res. 2010; Kuroda J et al., "NADPH oxidase 4 is a major source of oxidative stress in the failing heart" Proc Natl Acad Sci USA 2010). A connection between increased mitochondrial Nox4 activity and dysfunction of "the aging heart" has been suggested (Tetsuro Ago et al., AGING, December 2010, vol. 2 No 12).

Extracellular matrix accumulation contributes to the pathology of chronic kidney disease. The growth factor IGF-I activity is a major contributor to this process and Nox4 is a mediator in this process (New et al., Am J Physiol Cell Physiol. 302(1), 2012). The connection between chronic activation of the renin-angiotensin and the progression of kidney damage system is well established with Nox4 and Angiotensin II as collaborators in this process (Chen et al., Mol Cell Biol. 2012).

From the above, it thus appears that the Nox enzymes have several functions in the living body, and that they may also be involved in various disorders. Examples of such diseases and disorders are cardiovascular disorders, respiratory disorders, metabolism disorders, endocrine disorders, skin disorders, bone disorders, neuroinflammatory and/or neurodegenerative disorders, kidney diseases, reproduction disorders, diseases affecting the eye and/or the lens and/or conditions affecting the inner ear, inflammatory disorders, liver diseases, pain, cancers, allergic disorders, traumatisms, such as traumatic head injury, septic, hemorrhagic and anaphylactic shock, diseases or disorders of the gastrointestinal system, angiogenesis, angiogenesis-dependent conditions. It also appears that especially Nox4 has been found to be involved in such disorders. Consequently, it is considered that compounds capable of inhibiting Nox, and in particular compounds capable of selectively inhibiting Nox4, would be of great interest for use in the treatment of diseases and disorders involving Nox enzymes, and in particular Nox4.

Several patent applications from GenKyoTex SA relate to various pyrazolo and pyrazoline derivatives for use as Nox inhibitors. Thus, PCT applications WO 2010/035217, WO 2010/035219, WO 2010/035220, WO 2010/035221, WO 2011/036651, WO2011/101804 and WO2011/101805, describe several conditions and disorders related to Nox and provide references to various sources of literature on the subject. The information contained in said applications and in the literature referred to therein is incorporated herein by reference.

As noted herein above, Nox4 is involved in stroke, among other diseases. Stroke is the second leading cause of death worldwide and survivals often are disabled with serious cognitive difficulties affecting social life as well as the ability to perform work. In addition to the suffering of the patients and the close relatives this also is extremely costly to society and the healthcare system. Without new efficient treatment of stroke patients, the cost to care for stroke victims during the next 45 years will exceed $2.2 trillion in the US only.

Stroke is classified into two major categories. Ischemic that causes interruption of blood supply and hemorrhagic that results from rupture of a blood vessel. Both induce rapid loss of brain function caused by disturbances in blood supply. Ischemic stroke is by far the most common form accounting for 87% of the cases, while 9% are due to intracerebral hemorrhage and the remaining 4% are due to subarachnoid hemorrhage.

The pathophysiology of ischemic stroke is complex and the patient recovery is dependent on the length in time that neuronal tissues are deprived of blood supply. Brain tissues deprived of oxygen for more than three hours will be irreversibly damaged. The pathophysiology includes excitotoxicity mechanisms, inflammatory pathways, oxidative damage, ionic imbalances, apoptosis, angiogenesis and endogenous neuron protection. Additionally when white blood cells re-enter a previously hypo perfused region via returning blood, they can occlude small vessels, producing additional ischemia.

Different strategies to manage stroke are; to identify risk groups for preventive treatment; development, implantation and dissemination of evidence-based clinical practice guidelines in order to set a standard for stroke management through the continuum of care with early treatment that is fundamental to improve the outcome following an ischemic stroke attack. One of two approved treatments today is IV administration of tissue plasminogen activator (tPA) that will induce thrombolysis, which may remove the clot and restore blood supply to the brain tissue. The other method is to mechanically remove the clot, to restore blood supply. Other approaching methods are in early phase research and some in clinical trials. New potential therapies of interest include administration of neuroprotective agents, cooling of the ischemic brain and the use of stents to revasculate occluded arteries.

Thus, a method of treatment an ischemic stroke attack generally comprises removing mechanical hinders (blood clots) from the blood flow, e.g. by intravenous administration of tissue plasminogen activator (tPA). It is thought that combining the removal of mechanical hinders from the blood flow with administration, either before or after, of neuroprotective agents, may help saving ischemic neurons in the brain from irreversible injury, including apoptosis. However, as of today no neuroprotective agent has been provided for successful treatment of stroke. It therefore appears that there still is a need for improved treatment of stroke, in particular improved treatment by administration of neuroprotective agents, preferably in combination with the removal of blood clots in the ischemic brain.

SUMMARY OF THE INVENTION

According to one aspect, compounds are provided that are Nox inhibitors, for use in therapy. More specifically, compounds that are Nox4 inhibitors are provided for use in therapy. According to another aspect, compounds are provided that are effective in the treatment of diseases associated with, e.g. caused or driven by, elevated Nox activity, more specifically elevated Nox4 activity.

According to a further aspect, compounds are provided that are Nox inhibitors, more specifically Nox4 inhibitors, for use in the treatment of disorders, associated with elevated Nox activity, more specifically elevated Nox4 activity.

Thus, according to the present invention, a compound is provided of formula (I)

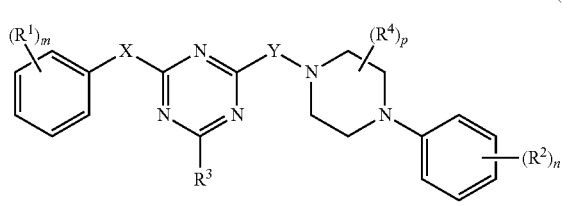

(I)

each $R^1$, $R^2$ and $R^3$ is independently selected from halogen, $R^5O(CH_2)_q$, $R^5S(CH_2)_q$, $R^6R^7N(CH_2)_q$, $CN(CH_2)_q$, C1-C6 alkyl, C2-C6 alkenyl, C2-C6 alkynyl, and C3-C6 cycloalkyl, said alkyl, alkenyl, alkynyl and cycloalkyl optionally being substituted with at least one halogen;
each $R^4$ is independently selected from halogen, C1-C6 alkyl, C2-C6 alkenyl, C2-C6 alkynyl, and C3-C6 cycloalkyl; said alkyl, alkenyl, alkynyl and cycloalkyl optionally being substituted with at least one halogen;
each $R^5$ is independently selected from H, C1-C6 alkyl, C2-C6 alkenyl, C2-C6 alkynyl, and C3-C6 cycloalkyl; said alkyl, alkenyl, alkynyl and cycloalkyl optionally being substituted with at least one halogen;
each $R^6$ and $R^7$ is independently selected from H, C1-C6 alkyl, C2-C6 alkenyl, C2-C6 alkynyl, and C3-C6 cycloalkyl; said alkyl, alkenyl, alkynyl and cycloalkyl optionally being substituted with at least one halogen;
X is NH, $CH_2$ or C(O);
Y is NH; $CH_2$ or C(O);
m is an integer of from 0 to 5;
n is an integer of from 0 to 5;
p is an integer of from 0 to 4; and
q is an integer of from 0 to 3;
or a pharmaceutically acceptable salt thereof,
for use in the treatment of a condition or disorder associated with Nox, preferably Nox4.

Examples of such conditions and disorders e.g. are those mentioned herein above as related to or mediated by Nox, for example conditions and disorders selected from cardiovascular disorders, endocrine disorders, respiratory disorders, metabolism disorders, skin disorders, bone disorders, neuroinflammatory and/or neurodegenerative disorders, kidney diseases, reproduction disorders, endocrine disorders, diseases affecting the eye and/or the lens and/or conditions affecting the inner ear, inflammatory disorders, liver diseases, pain, cancers, allergic disorders, traumatisms, septic, hemorrhagic and anaphylactic shock, diseases or disorders of the gastrointestinal system, angiogenesis, angiogenesis-dependent conditions, as well as lung infections, acute lung injury, pulmonary arterial hypertension, obstructive lung disorders, fibrotic lung disease, and lung cancer.

According to one aspect, there is provided a method of inhibiting the activity of Nox, in particular Nox4, in a mammal in need thereof, by administering to said mammal a compound of formula (I) as defined herein above.

According to one aspect, the compounds of the present invention are for use as neuroprotective agents in the treatment of stroke, e.g. ischemic stroke.

According to one aspect, the use of a compound as defined herein is provided, for the manufacturing of a medicament for the treatment of any of the disorders mentioned herein.

According to one aspect, there is provided a compound selected from

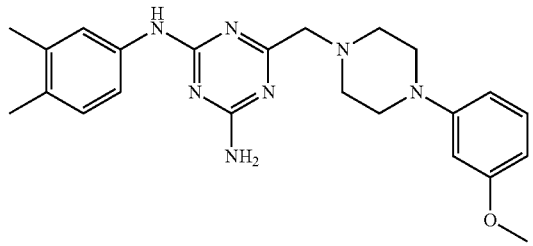

$N^2$-(3,4-dimethylphenyl)-6-((4-(3-methoxyphenyl)piperazin-1-yl)methyl)-1,3,5-triazine-2,4-diamine;

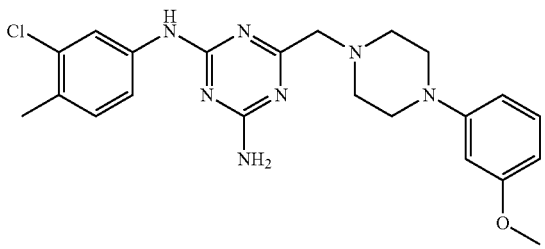 [SMILES: COc1cccc(N2CCN(Cc3nc(N)nc(Nc4ccc(C)c(Cl)c4)n3)CC2)c1]

$N^2$-(3-chloro-4-methylphenyl)-6-((4-(3-methoxyphenyl)piperazin-1-yl)methyl)-1,3,5-triazine-2,4-diamine;

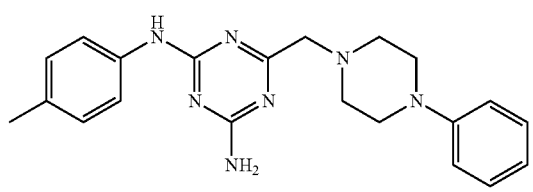 [SMILES: Cc1ccc(Nc2nc(N)nc(CN3CCN(c4ccccc4)CC3)n2)cc1]

6-((4-phenylpiperazin-1-yl)methyl)-$N^2$-(p-tolyl)-1,3,5-triazine-2,4-diamine;

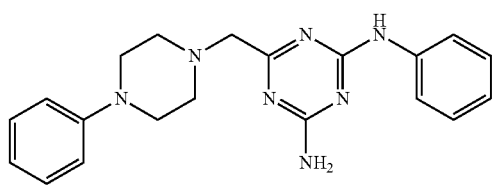 [SMILES: Nc1nc(CN2CCN(c3ccccc3)CC2)nc(Nc2ccccc2)n1]

$N^2$-phenyl-6-((4-phenylpiperazin-1-yl)methyl)-1,3,5-triazine-2,4-diamine;

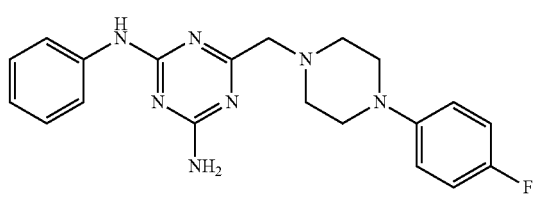 [SMILES: Nc1nc(CN2CCN(c3ccc(F)cc3)CC2)nc(Nc2ccccc2)n1]

6-((4-(4-fluorophenyl)piperazin-1-yl)methyl)-$N^2$-phenyl-1,3,5-triazine-2,4-diamine;
or a pharmaceutically acceptable salt thereof, for use in therapy.

In another aspect, a pharmaceutical composition is provided, comprising

N²-(3,4-dimethylphenyl)-6-((4-(3-methoxyphenyl)piperazin-1-yl)methyl)-1,3,5-triazine-2,4-diamine;
N²-(3-chloro-4-methylphenyl)-6-((4-(3-methoxyphenyl)piperazin-1-yl)methyl)-1,3,5-triazine-2,4-diamine;
6-((4-phenylpiperazin-1-yl)methyl)-N²-(p-tolyl)-1,3,5-triazine-2,4-diamine;
N²-phenyl-6-((4-phenylpiperazin-1-yl)methyl)-1,3,5-triazine-2,4-diamine; or
6-((4-(4-fluorophenyl)piperazin-1-yl)methyl)-N²-phenyl-1,3,5-triazine-2,4-diamine;

or a pharmaceutically acceptable salt thereof and optionally at least one pharmaceutically acceptable excipient.

DETAILED DESCRIPTION OF THE INVENTION

Figure 1:
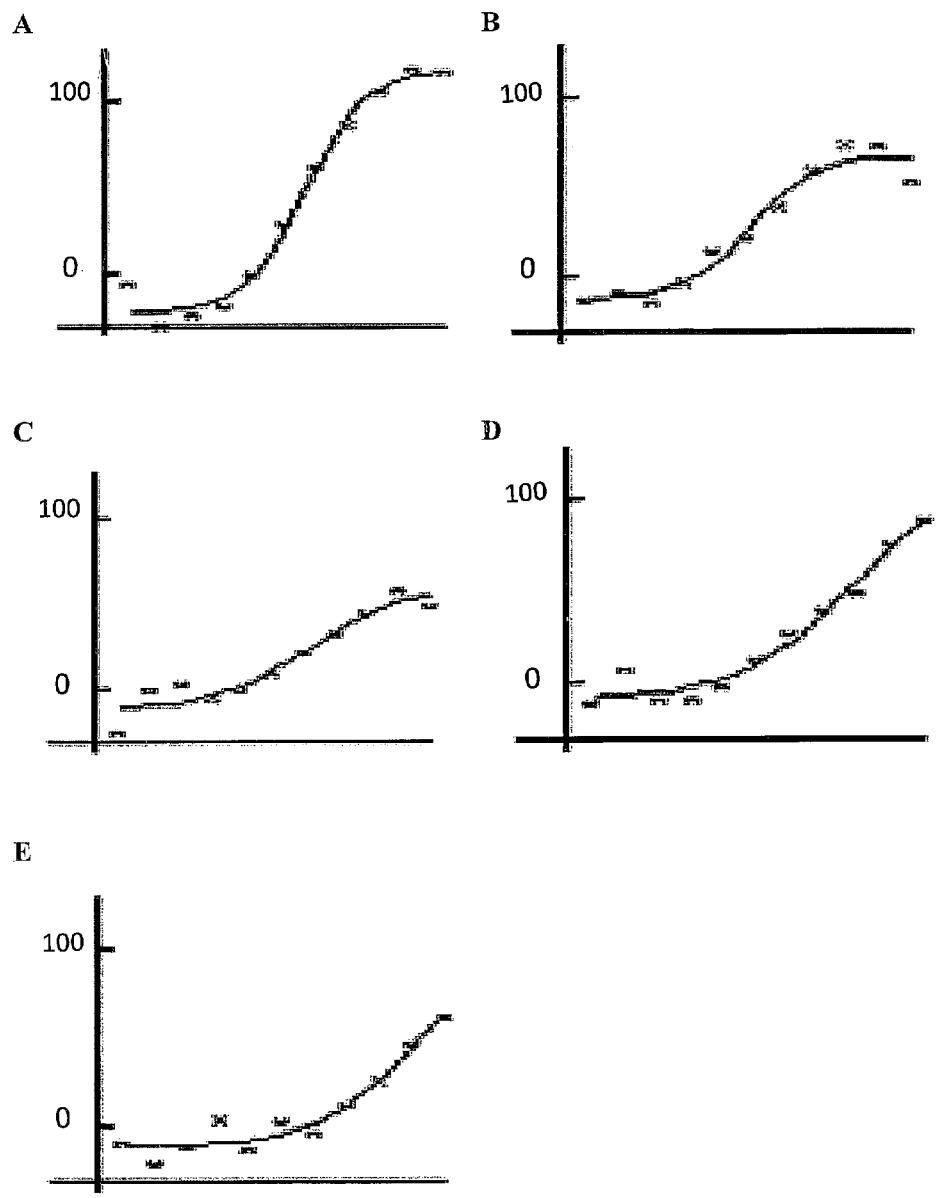
FIG. 1 shows dose-response curves for 4 different compounds of the invention in Nox4-transfected TRex-293 cells, at 11 concentrations obtained by serial dilution 1:3 of a 200 μM solution of tested compound: A) N²-(3,4-dimethylphenyl)-6-((4-(3-methoxyphenyl)piperazin-1-yl)methyl)-1,3,5-triazine-2,4-diamine, B) N²-(3-chloro-4-methylphenyl)-6-((4-(3-methoxyphenyl)piperazin-1-yl)methyl)-1,3,5-triazine-2,4-diamine, C) 6-((4-phenylpiperazin-1-yl)methyl)-N²-(p-tolyl)-1,3,5-triazine-2,4-diamine, D) N²-phenyl-6-((4-phenylpiperazin-1-yl)methyl)-1,3,5-triazine-2,4-diamine, and E) 6-((4-(4-fluorophenyl)piperazin-1-yl)methyl)-N²-phenyl-1,3,5-triazine-2,4-diamine.

In general any term used herein shall be given its normal meaning as accepted within the field to which the present invention belongs. For the sake of clarity, however, some definitions will be given herein below, and shall apply throughout the specification and the appended claims, unless otherwise specified or apparent from the context.

The term "endocrine disorder" refers to disorders of the endocrine system and may be as well endocrine gland hyposecretion as hypersecretion, or tumors of endocrine glands. Diabetes and polycystic ovarian syndrome are examples of endocrine disorders.

The term "cardiovascular disorder or disease" comprises atherosclerosis, especially diseases or disorders associated with endothelial dysfunction including but not limited to hypertension, cardiovascular complications of Type I or Type II diabetes, intimal hyperplasia, coronary heart disease, cerebral, coronary or arterial vasospasm, endothelial dysfunction, heart failure including congestive heart failure, peripheral artery disease, restenosis, trauma caused by a stent, stroke, ischemic attack, vascular complications such as after organ transplantation, myocardial infarction, hypertension, formation of atherosclerotic plaques, platelet aggregation, angina pectoris, aneurysm, aortic dissection, ischemic heart disease, cardiac hypertrophy, pulmonary embolus, thrombotic events including deep vein thrombosis, injury caused after ischemia by restoration of blood flow or oxygen delivery as in organ transplantation, open heart surgery, angioplasty, hemorrhagic shock, angioplasty of ischemic organs including heart, brain, liver, kidney, retina and bowel.

The term "respiratory disorder or disease" comprises bronchial asthma, bronchitis, allergic rhinitis, adult respiratory syndrome, cystic fibrosis, lung viral infection (influenza), pulmonary hypertension, idiopathic pulmonary fibrosis and chronic obstructive pulmonary diseases (COPD).

The term "allergic disorder" includes hay fever and asthma.

The term "traumatism" includes polytraumatism.

The term "disease or disorder affecting the metabolism" includes obesity, metabolic syndrome and Type II diabetes.

The term "skin disease" or disorder" includes psoriasis, eczema, dermatitis, wound healing and scar formation.

The term "bone disorder" includes osteoporosis, osteoporasis, osteosclerosis, periodontitis, and hyperparathyroidism.

The term "neurodegenerative disease or disorder" comprises a disease or a state characterized by a central nervous system (CNS) degeneration or alteration, especially at the level of the neurons such as Alzheimer's disease, Parkinson's disease, Huntington's disease, amyotrophic lateral sclerosis, epilepsy and muscular dystrophy. It further comprises neuro-inflammatory and demyelinating states or diseases such as leukoencephalopathies, and leukodystrophies.

The term "demyelinating" is referring to a state or a disease of the CNS comprising the degradation of the myelin around the axons. In the context of the invention, the term demyelinating disease is intended to comprise conditions which comprise a process that demyelinate cells such as multiple sclerosis, progressive multifocal leukoencephalopathy (PML), myelopathies, any neuroinflammatory condition involving autoreactive leukocyte within the CNS, congenital metabolic disorder, a neuropathy with abnormal myelination, drug induced demyelination, radiation induced demyelination, a hereditary demyelinating condition, a prion induced demyelinating condition, encephalitis induced demyelination or a spinal cord injury. Preferably, the condition is multiple sclerosis.

The term "kidney disease or disorder" includes diabetic nephropathy, renal failure, glomerulonephritis, nephrotoxicity of aminoglycosides and platinum compounds and hyperactive bladder. In a particular embodiment, the term according to the invention includes chronic kidney diseases or disorders.

The term "reproduction disorder or disease" includes erectile dysfunction, fertility disorders, prostatic hypertrophy and benign prostatic hypertrophy.

The term "disease or disorder affecting the eye and/or the lens" includes cataract including diabetic cataract, re-opacification of the lens post cataract surgery, diabetic and other forms of retinopathy.

The term "conditions affecting the inner ear" includes presbyacusis, tinnitus, Meniere's disease and other balance problems, utriculolithiasis, vestibular migraine, and noise induced hearing loss and drug induced hearing loss (ototoxicity).

The term "inflammatory disorder or disease" means inflammatory bowel disease, sepsis, septic shock, adult respiratory distress syndrome, pancreatitis, shock induced by trauma, bronchial asthma, allergic rhinitis, rheumatoid arthritis, chronic rheumatoid arthritis, arteriosclerosis, intracerebral hemorrhage, cerebral infarction, heart failure, myocardial infarction, psoriasis, cystic fibrosis, stroke, acute bronchitis, chronic bronchitis, acute bronchiolitis, chronic bronchiolitis, osteoarthritis, gout, myelitis, ankylosing spondylitis, Reuter syndrome, psoriatic arthritis, spondylarthritis, juvenile arthritis or juvenile ankylosing spondylitis, reactive arthritis, infectious arthritis or arthritis after infection, gonococcal arthritis, syphilitic arthritis, Lyme disease, arthritis induced by "angiitis syndrome," polyarteritis nodosa, anaphylactic angiitis, Luegenec granulomatosis, rheumatoid polymyalgia, articular cell rheumatism, calcium crystal deposition arthritis, pseudogout, non-arthritic rheumatism, bursitis, tendosynovitis, epicondyle inflammation (tennis elbow), carpal tunnel syndrome, disorders by repetitive use (typing), mixed form of arthritis, neuropathic arthropathy, hemorrhagic arthritis, vascular peliosis, hypertrophic osteoarthropathy, multicentric reticulohistiocytosis, arthritis induced by specific diseases, blood pigmentation, sickle cell disease and other hemoglobin abnormality, hyperlipoproteinemia, dysgammaglobulinemia, hyperparathyroidism, acromegaly, familial Mediterranean fever, Bechet's disease, systemic autoimmune disease erythematosus, multiple sclerosis and Crohn's disease or diseases like relapsing polychondritis, chronic inflammatory bowel diseases (IBD) or the related diseases which require the administration to a mammal in a therapeutic effective dose of a compound expressed by Formula (I) in a sufficient dose to inhibit NADPH oxidase.

The term "liver diseases or disorders" include liver fibrosis, alcohol induced fibrosis, steatosis and non-alcoholic steatohepatitis.

The term "arthritis" means acute rheumatic arthritis, chronic rheumatoid arthritis, chlamydial arthritis, chronic absorptive arthritis, anchylous arthritis, arthritis based on bowel disease, filarial arthritis, gonorrheal arthritis, gouty arthritis, hemophilic arthritis, hypertrophic arthritis, juvenile chronic arthritis, Lyme arthritis, neonatal foal arthritis, nodular arthritis, ochronotic arthritis, psoriatic arthritis or suppurative arthritis, or the related diseases which require the administration to a mammal in a therapeutic effective dose of a compound expressed by Formula (I) in a sufficient dose to inhibit NADPH oxidase.

The term "pain" includes hyperalgesia associated with inflammatory pain.

The term "cancer" means carcinoma (e.g., fibrosarcoma, myxosarcoma, liposarcoma, chondrosarcoma, osteogenic sarcoma, chordoma, angiosarcoma, endothelium sarcoma, lymphangiosarcoma, lymphangioendothelioma, periosteoma, mesothelioma, Ewing's tumor, leiomyosarcoma, rhabdomyosarcoma, colon carcinoma, pancreatic cancer, breast cancer, ovarian cancer, renal cancer, prostatic carcinoma, squamous cell carcinoma, basal cell carcinoma, adenocarcinoma, sweat gland carcinoma, sebaceous gland carcinoma, papillary carcinoma, papillary adenocarcinoma, cystadenocarcinoma, medullary carcinoma, bronchogenic carcinoma, renal cell carcinoma, hepatocellular carcinoma, cholangiocarcinoma, choriocarcinoma, seminoma, embryonal carcinoma, Wilms' tumor, cervical cancer, orchioncus, lung cancer, small-cell lung cancer, lung adenocarcinoma, bladder cancer or epithelial cancer) or the related diseases which require the administration to a mammal in a therapeutic effective dose of a compound expressed by the Formula (I) in a sufficient dose to inhibit NADPH oxidase.

The term "disease or disorders of the gastrointestinal system", includes gastric mucosa disorders ischemic bowel disease management, enteritis/colitis, cancer chemotherapy, or neutropenia.

The term "angiogenesis" includes sprouting angiogenesis, intussusceptive angiogenesis, vasculogenesis, arteriogenesis and lymphangiogenesis. Angiogenesis is the formation of new blood vessels from pre-existing capillaries or post-capillary venules and occurs in pathological conditions such as cancers, arthritis and inflammation. A large variety of tissues, or organs comprised of organized tissues, can support angiogenesis in disease conditions including skin, muscle, gut, connective tissue, joints, bones and the like tissue in which blood vessels can invade upon angiogenic stimuli. As used herein, the term "angiogenesis-dependent condition" is intended to mean a condition where the process of angiogenesis or vasculogenesis sustains or augments a pathological condition. Vasculogenesis results from the formation of new blood vessels arising from angioblasts which are endothelial cell precursors. Both processes result in new blood vessel formation and are included in the meaning of the term angiogenesis-dependent conditions. Similarly, the term "angiogenesis" as used herein is intended to include de novo formation of vessels such as those arising from vasculogenesis as well as those arising from branching and sprouting of existing vessels, capillaries and venules.

The term "angiogenesis inhibitory," means which is effective in the decrease in the extent, amount, or rate of neovascularization. Effecting a decrease in the extent, amount, or rate of endothelial cell proliferation or migration in the tissue is a specific example of inhibiting angiogenesis. Angiogenesis inhibitory activity is particularly useful in the treatment of any cancers as it targets tumor growth process and in the absence of neovascularization of tumor tissue, the tumor tissue does not obtain the required nutrients, slows in growth, ceases additional growth, regresses and ultimately becomes necrotic resulting in killing of the tumor. Further, an angiogenesis inhibitory activity is particularly useful in the treatment of any cancers as it is particularly effective against the formation of metastases because their formation also requires vascularization of a primary tumor so that the metastatic cancer cells can exit the primary tumor and their establishment in a secondary site requires neovascularization to support growth of the metastases.

As used herein, "treatment" and "treating" and the like generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it; (b) inhibiting the disease, i.e., arresting its development; or relieving the disease, i.e., causing regression of the disease and/or its symptoms or conditions.

The term "subject" as used herein refers to mammals. For examples, mammals contemplated by the present invention include human, primates, domesticated animals such as cattle, sheep, pigs, horses and the like.

"An effective amount" refers to an amount of a compound that confers a therapeutic effect on the treated subject. The therapeutic effect may be objective (i.e., measurable by some test or marker) or subjective (i.e., subject gives an indication of or feels an effect).

The term "inhibitor" used in the context of the invention is defined as a molecule that inhibits completely or partially the activity of Nox, in particular Nox4, and/or inhibits or reduces the generation of reactive oxygen species (ROS).

"Pharmaceutically acceptable" means being useful in preparing a pharmaceutical composition that is generally safe, non-toxic and neither biologically nor otherwise undesirable and includes being useful for veterinary use as well as human pharmaceutical use.

The term Cn, where n is an integer, specifies that a radical or moiety contains n carbon atoms. The term Cn–Cm, where m and n are both integers, and m>n, refers to a radical or moiety containing n, n+1, n+2, . . . or m carbon atoms. Thus, the term C1-C6 alkyl refers to an alkyl radical that may contain 1, 2, 3, 4, 5 or 6 carbon atoms. The term C0 alkyl refers to a covalent bond.

An alkyl moiety according to the invention may be branched or linear, e.g. selected from methyl, ethyl, n-propyl, i-propyl, n-butyl, i-butyl, sec-butyl, tert-butyl, n-pentyl, 2-methylbutyl, 2,2-dimethylpropyl, n-hexyl, 2-methylpentyl, 3-methylpentyl, 2,2-dimethylbutyl, and 2,3-dimethylbutyl.

A C1-C6 alkyl according to the invention more particularly may be selected from C1-05 alkyl, e.g. from C1-C4 alkyl, from C1-C3 alkyl, from C1-C2 alkyl, or may be methyl.

The term "C2-C6 alkenyl" refers to a straight or branched chain alkenyl having from 2 to 6 carbon atoms in the chain and that may have any available number of double bonds in any available positions. The configuration of the double bond may be (E) or (Z). Examples are vinyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, and 5-hexenyl. A C2-C6 alkenyl according to the invention, more specifically may be a C2-C4 alkenyl, or a C2-C3 alkenyl.

The term "C2-C6 alkynyl" refers to a straight or branched chain alkynyl having from 2 to 6 carbon atoms in the chain and that may have any available number of triple bonds in any available positions. Examples are ethynyl, 1-propynyl, 2-propynyl, 2-butynyl, and 2-pentene-4-ynyl. A C2-C6 alkynyl according to the invention, more specifically may be a C2-C4 alkynyl, or a C2-C3 alkynyl.

The term "C3-C6 cycloalkyl" refers to a cyclic alkyl radical having from 3 to 6 ring carbon atoms, such as cyclopropyl, cyclobutyl, cyclopentyl or cyclohexyl.

By "substituted with at least one halogen" is meant that at least one hydrogen is replaced by a halogen, e.g. F. An example of an alkyl substituted with at least one halogen is trifluoromethyl.

As used herein, and unless otherwise specified, the term "halogen" (or "halo") means fluorine (F), chlorine (Cl), bromine (Br) or iodine (I). Any halogen according to the invention more particularly may be selected from F and Cl.

In a compound of formula (I) as provided herein, each $R^1$, $R^2$ and $R^3$ is independently selected from halogen, $R^5O(CH_2)_q$, $R^5S(CH_2)_q$, $R^6R^7N(CH_2)_q$, $CN(CH_2)_q$, C1-C6 alkyl, C2-C6 alkenyl, C2-C6 alkynyl, and C3-C6 cycloalkyl, said alkyl, alkenyl, alkynyl and cycloalkyl optionally being substituted with at least one halogen.

In some embodiments, each $R^1$, $R^2$ and $R^3$ is independently selected from halogen, $R^5O(CH_2)_q$, $R^5S(CH_2)_q$, $R^6R^7N(CH_2)_q$, and C1-C6 alkyl, said alkyl, optionally being substituted with at least one halogen.

In some other embodiments, each $R^1$, $R^2$ and $R^3$ is independently selected from halogen, $R^5O(CH_2)_q$, $R^6R^7N(CH_2)_q$, and C1-C6 alkyl, said alkyl, optionally being substituted with at least one halogen.

As noted herein above, each $R^1$ is independently selected from halogen, $R^5O(CH_2)_q$, $R^5S(CH_2)_q$, $R^6R^7N(CH_2)_q$, $CN(CH_2)_q$, C1-C6 alkyl, C2-C6 alkenyl, C2-C6 alkynyl, and C3-C6 cycloalkyl, said alkyl, alkenyl, alkynyl and cycloalkyl optionally being substituted with at least one halogen.

In some embodiments, each $R^1$ is independently selected from halogen, $R^5O(CH_2)_q$, $R^5S(CH_2)_q$, $CN(CH_2)_q$, C1-C6 alkyl, C2-C6 alkenyl, C2-C6 alkynyl, and C3-C6 cycloalkyl, said alkyl, alkenyl, alkynyl and cycloalkyl optionally being substituted with at least one halogen.

In some other embodiments, each $R^1$ is independently selected from halogen, $R^5O(CH_2)_q$, $R^5S(CH_2)_q$, C1-C6 alkyl, C2-C6 alkenyl, C2-C6 alkynyl, and C3-C6 cycloalkyl, said alkyl, alkenyl, alkynyl and cycloalkyl optionally being substituted with at least one halogen.

In still other embodiments, each $R^1$ is independently selected from halogen, C1-C6 alkyl, C2-C6 alkenyl, C2-C6 alkynyl, and C3-C6 cycloalkyl, said alkyl, alkenyl, alkynyl and cycloalkyl optionally being substituted with at least one halogen.

In some particular embodiments, each $R^1$ is independently selected from halogen and C1-C6 alkyl, said alkyl optionally being substituted with at least one halogen.

In some embodiments, each $R^1$ is independently selected from C1-C6 alkyl, said alkyl optionally being substituted with at least one halogen.

In some embodiments, each $R^1$ is independently selected from halogen.

In any of the above embodiments, when $R^1$ is halogen, it especially may be selected from F and Cl, and in particular $R^1$ may be Cl.

As noted herein above, each $R^2$ is independently selected from halogen, $R^5O(CH_2)_q$, $R^5S(CH_2)_q$, $R^6R^7N(CH_2)_q$, $CN(CH_2)_q$, C1-C6 alkyl, C2-C6 alkenyl, C2-C6 alkynyl, and C3-C6 cycloalkyl, said alkyl, alkenyl, alkynyl and cycloalkyl optionally being substituted with at least one halogen.

In some embodiments, each $R^2$ is independently selected from halogen, $R^5O(CH_2)_q$, $R^5S(CH_2)_q$, $CN(CH_2)_q$, C1-C6 alkyl, C2-C6 alkenyl, C2-C6 alkynyl, and C3-C6 cycloalkyl, said alkyl, alkenyl, alkynyl and cycloalkyl optionally being substituted with at least one halogen.

In some other embodiments, each $R^2$ is independently selected from halogen, $R^5O(CH_2)_q$, $R^5S(CH_2)_q$, C1-C6 alkyl, C2-C6 alkenyl, C2-C6 alkynyl, and C3-C6 cycloalkyl, said alkyl, alkenyl, alkynyl and cycloalkyl optionally being substituted with at least one halogen.

In still other embodiments, each $R^2$ is independently selected from halogen, $R^5O(CH_2)_q$, $R^5S(CH_2)_q$, and C1-C6 alkyl, said alkyl optionally being substituted with at least one halogen.

In further embodiments, each $R^2$ is independently selected from halogen, $R^5O(CH_2)_q$, and $R^5S(CH_2)_q$.

In some embodiments, each $R^2$ is independently selected from $R^5O(CH_2)_q$, and $R^5S(CH_2)_q$.

In some other embodiments, each $R^2$ is independently selected from halogen, and $R^5O(CH_2)_q$.

In some embodiments, each $R^2$ is independently selected from $R^5O(CH_2)_q$.

In some other embodiments, each $R^2$ is independently selected from halogen.

As noted herein above, $R^3$ is independently selected from halogen, $R^5O(CH_2)_q$, $R^5S(CH_2)_q$, $R^6R^7N(CH_2)_q$, $CN(CH_2)_q$, C1-C6 alkyl, C2-C6 alkenyl, C2-C6 alkynyl, and C3-C6 cycloalkyl, said alkyl, alkenyl, alkynyl and cycloalkyl optionally being substituted with at least one halogen.

In some embodiments, $R^3$ is independently selected from halogen, $R^5O(CH_2)_q$, $R^5S(CH_2)_q$, $R^6R^7N(CH_2)_q$, $CN(CH_2)_q$, C1-C6 alkyl, said alkyl optionally being substituted with at least one halogen.

In some other embodiments, $R^3$ is $R^6R^7N(CH_2)_q$.

In a compound of formula (I), each $R^4$ is independently selected from halogen, e.g. F, C1-C6 alkyl, C2-C6 alkenyl, C2-C6 alkynyl, and C3-C6 cycloalkyl; said alkyl, alkenyl, alkynyl and cycloalkyl optionally being substituted with at least one halogen.

In some embodiments, each $R^4$ is independently selected from halogen, e.g. F and C1-C6 alkyl, said alkyl, optionally being substituted with at least one halogen.

In a compound of formula (I), any $R^5$, when present, is independently selected from H, C1-C6 alkyl, C2-C6 alkenyl, C2-C6 alkynyl, and C3-C6 cycloalkyl; said alkyl, alkenyl, alkynyl and cycloalkyl optionally being substituted with at least one halogen.

In some embodiments, any $R^5$, when present, is independently selected from C1-C6 alkyl, C2-C6 alkenyl, C2-C6 alkynyl, and C3-C6 cycloalkyl; said alkyl, alkenyl, alkynyl and cycloalkyl optionally being substituted with at least one halogen.

In some embodiments, any $R^5$, when present, is independently selected from H and C1-C6 alkyl, said alkyl optionally being substituted with at least one halogen.

In some embodiments, any $R^5$, when present, is independently selected from C1-C6 alkyl, said alkyl optionally being substituted with at least one halogen.

In a compound of formula (I), each $R^6$ and $R^7$ is independently selected from H, C1-C6 alkyl, C2-C6 alkenyl, C2-C6 alkynyl, and C3-C6 cycloalkyl; said alkyl, alkenyl, alkynyl and cycloalkyl optionally being substituted with at least one halogen.

In some embodiments, each $R^6$ and $R^7$ is independently selected from H and C1-C6 alkyl, said alkyl optionally being substituted with at least one halogen.

In some embodiments, $R^6$ is as defined herein above and $R^7$ is H. In other embodiments, both $R^6$ and $R^7$ are H.

In a compound of formula (I) as defined herein, X is NH, $CH_2$ or C(O). In some embodiments, X is NH or $CH_2$. In other embodiments, X is NH.

In a compound of formula (I) as defined herein, Y is NH, $CH_2$ or C(O). In some embodiments, Y is NH or $CH_2$. In other embodiments, Y is $CH_2$.

The integer m, representing the number of moieties $R^1$ in a compound of formula (I), ranges from 0 to 5, from 0 to 4, from 0 to 3, or from 0 to 2. In some embodiments, m is at least 1, e.g. m is 1-5, 1-4, or 1-3. In some embodiments, m is 1 or 2, e.g. m is 2.

In some embodiments, when m is an integer of 1 or higher, one $R^1$ is attached to the phenyl ring in para position or in meta position. In other words, the phenyl ring is substituted on any of carbon atoms number 3, 4 or 5 of the phenyl ring, assuming that the X link to the triazine ring is attached at carbon atom number 1 of the phenyl ring.

In some embodiments, when m is an integer of 1 or higher, one $R^1$ is attached to the phenyl ring in para position.

In some embodiments, when m is an integer of 2 or higher, one $R^1$ is attached to the phenyl ring in para position and one $R^1$ is attached in meta position.

The integer n, representing the number of moieties $R^2$ in a compound of formula (I), ranges from 0 to 5, from 0 to 4, from 0 to 3, or from 0 to 2. In some embodiments, n is at least 1, e.g. n is 1-5, 1-4, or 1-3. In some embodiments, n is 1 or 2, e.g. n is 1. In some embodiments, n is 0 or 1.

In some embodiments, when n is an integer of 1 or higher, one $R^2$ is attached to the phenyl ring in para position or in meta position. In other words, the phenyl ring is substituted on any of carbon atoms number 3, 4 or 5 of the phenyl ring, assuming that the Y link to the triazine ring is attached at carbon atom number 1 of the phenyl ring.

In some embodiments, when n is an integer of 1 or higher, e.g. n is 1, one $R^2$ is attached to the phenyl ring in meta position, e.g. $R^2$ is $R^5O(CH_2)_q$ in meta position. For example, n is 1 and $R^2$ is in meta position and is $R^5O(CH_2)_q$.

In some embodiments, when n is an integer of 1 or higher, e.g. n is 1, one $R^2$ is attached to the phenyl ring in para position, e.g. $R^2$ is a halogen, such as F, in para position.

The integer p, representing the number of moieties $R^4$ in a compound of formula (I), ranges from 0 to 4, from 0 to 3, or from 0 to 2, e.g. p is 0 or 1. In some embodiments, p is 0.

The integer q in any moiety $R^5O(CH_2)_q$, $R^5S(CH_2)_q$, $R^6R^7N(CH_2)_q$, and $CN(CH_2)_q$ is selected from 0, 1, 2 and 3. In some embodiments, any q is selected from 0, 1 and 2; or from 0 and 1. In some embodiments, q is 0, i.e. any moiety $R^5O(CH_2)_q$, $R^5S(CH_2)_q$, $R^6R^7N(CH_2)_q$, or $CN(CH_2)_q$ is $R^5O-$, $R^5S-$, $R^6R^7N-$, or $CN-$.

In some particular embodiments, X is NH and Y is $CH_2$. In some other particular embodiments, X is NH, Y is $CH_2$, and p is 0. In still other particular embodiments, X is NH, Y is $CH_2$, p is 0, and $R^3$ is $R^6R^7N$.

Many further embodiments are possible and contemplated within the scope of formula (I), some of which are illustrated in a non-limiting fashion in the following Table 1.

TABLE 1

Exemplary embodiments of a compound of formula (I) according to the invention

| Special feature(s) of embodiment | Structural formula of embodiment |
|---|---|
| (a) X is NH | (Ia) |

TABLE 1-continued

Exemplary embodiments of a compound of formula (I) according to the invention

| Special feature(s) of embodiment | Structural formula of embodiment |
|---|---|
| (b) Y is $CH_2$ | (Ib) |
| (C) $R^3$ is $NR^6R^7(CH_2)q$ | (Ic) |
| (d) p is 0 | (Id) |
| (e) m is at least 1, and one $R^1$ is in para position | (Ie) |
| (f) n is at least 1, and one $R^2$ is in meta position | (If) |
| (g) $R^3$ is $NR^6R^7(CH_2)q$, and q is 0 | (Ig) |

TABLE 1-continued
Exemplary embodiments of a compound of formula (I) according to the invention
| Special feature(s) of embodiment | Structural formula of embodiment |
|---|---|
| (h) = (a) + (b) | 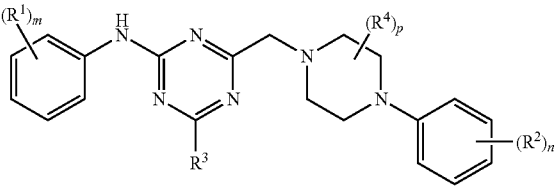 (Ih) |
| (i) = (h) + (c) | 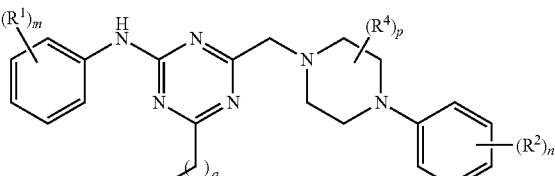 (Ii) |
| (j) = (i) + (d) | 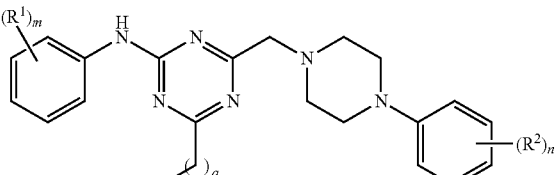 (Ij) |
| (k) = (h) + (g) | 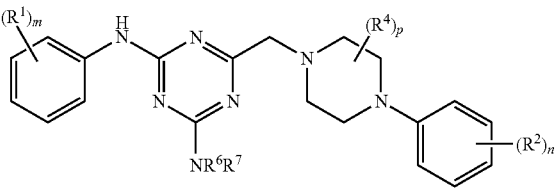 (Ik) |
| (m) = (k) + (d) | 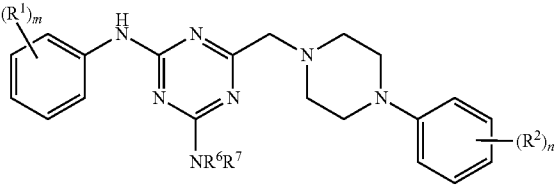 (Im) |
| (n) = (m) wherein $R^6$ and $R^7$ are both H | 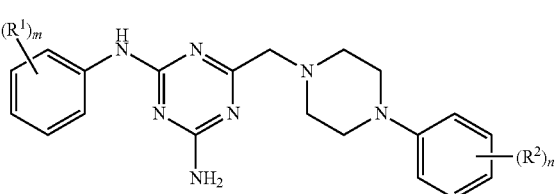 (In) |

In Table 1 the sum of e.g. (a) and (b), written as (h)=(a)+(b), refers to an embodiment ("embodiment (h)") comprising the features of embodiments (a) and (b), respectively, i.e. wherein X has been specified as NH, and Y has been specified as $CH_2$, and so on with other embodiments.

Unless apparent from the context or specified herein, any reference to a compound of formula (I) also is intended as applying to a compound any one of the formulas (Ia) to (In), as illustrated in Table 1. It should however be realized that many other embodiments are also possible within the scope of the invention.

In some particular embodiments, the compound of the invention is selected from $N^2$-(3,4-dimethylphenyl)-6-((4-(3-methoxyphenyl)piperazin-1-yl)methyl)-1,3,5-triazine-2,4-diamine;

$N^2$-(3-chloro-4-methylphenyl)-6-((4-(3-methoxyphenyl)piperazin-1-yl)methyl)-1,3,5-triazine-2,4-diamine;

6-((4-phenylpiperazin-1-yl)methyl)-$N^2$-(p-tolyl)-1,3,5-triazine-2,4-diamine;

$N^2$-phenyl-6-((4-phenylpiperazin-1-yl)methyl)-1,3,5-triazine-2,4-diamine; and 6-((4-(4-fluorophenyl)piperazin-1-yl)methyl)-$N^2$-phenyl-1,3,5-triazine-2,4-diamine; or from pharmaceutically acceptable salts thereof.

The compounds of formula (I) can be prepared by methods well known in the art, from readily available starting materials using general methods and procedures. Some compounds of formula (I) may be commercially available, e.g. from Vitas laboratories, Moscow, 125252, Russia.

The compounds of the present invention are Nox inhibitors. More specifically, the compounds of the present invention are Nox4 inhibitors. The capacity of inhibiting predominantly one particular Nox iso form, i.e. Nox4, is considered to be an important advantage of the present compounds, in view of the fact that Nox isoforms not only are involved in diseases, as Nox4, but also have various important biological functions in the living body.

Depending on the process conditions the end products of formula (I) are obtained either in neutral or salt form. Both the free base and the free acid, as well as the salts of these end products are within the scope of the invention. Acid addition salts of the inventive compounds may in a manner known per se be transformed into the free base using basic agents such as alkali or by ion exchange. The free base obtained may also form salts with organic or inorganic acids. Alkali addition salts of the inventive compounds may in a manner known per se be transformed into the free acid by using acidic agents such as acid or by ion exchange. The free acid obtained may also form salts with organic or inorganic bases.

In the preparation of acid or base addition salts, preferably such acids or bases are used which form suitably therapeutically acceptable salts. Examples of such acids are hydrohalogen acids, sulfuric acid, phosphoric acid, nitric acid, aliphatic, alicyclic, aromatic or heterocyclic carboxylic or sulfonic acids, such as formic acid, acetic acid, propionic acid, succinic acid, glycolic acid, lactic acid, malic acid, tartaric acid, citric acid, ascorbic acid, maleic acid, hydroxymaleic acid, pyruvic acid, p-hydroxybenzoic acid, embonic acid, methanesulfonic acid, ethanesulfonic acid, hydroxyethanesulfonic acid, halogenbenzenesulfonic acid, toluenesulfonic acid or naphthalenesulfonic acid. Base addition salts include those derived from inorganic bases, such as ammonium or alkali or alkaline earth metal hydroxides, carbonates, bicarbonates, and the like, and organic bases such as alkoxides, alkyl amides, alkyl and aryl amines, and the like. Examples of bases useful in preparing salts of the present invention include sodium hydroxide, potassium hydroxide, ammonium hydroxide, potassium carbonate, and the like.

There may be several stereoisomers of the compounds of the invention, including enantiomers and diastereomers. Enantiomers can be present in their pure forms, or as racemic (equal) or unequal mixtures of two enantiomers. Diastereomers can be present in their pure forms, or as mixtures of diastereomers. Diastereomers also include geometric isomers, which can be present in their pure cis or trans forms or as mixtures of those.

Pharmaceutical formulations are usually prepared by mixing the active substance, i.e. a compound of the invention, or a pharmaceutically acceptable salt thereof, with conventional pharmaceutical excipients. The formulations can be further prepared by known methods such as granulation, compression, microencapsulation, spray coating, etc. The formulations may be prepared by conventional methods in the dosage form of tablets, capsules, granules, powders, syrups, suspensions, suppositories or injections. Liquid formulations may be prepared by dissolving or suspending the active substance in water or other suitable vehicles. Tablets and granules may be coated in a conventional manner.

For clinical use, the compounds of the invention are formulated into pharmaceutical formulations for oral, rectal, parenteral or other mode of administration. These pharmaceutical preparations are a further object of the invention.

Usually the effective amount of active compounds is between 0.1-95% by weight of the preparation, preferably between 0.2-20% by weight in preparations for parenteral use and preferably between 1 and 50% by weight in preparations for oral administration.

The dose level and frequency of dosage of the specific compound will vary depending on a variety of factors including the potency of the specific compound employed, the metabolic stability and length of action of that compound, the patient's age, body weight, general health, sex, diet, mode and time of administration, rate of excretion, drug combination, the severity of the condition to be treated, and the patient undergoing therapy. The daily dosage may, for example, range from about 0.001 mg to about 100 mg per kilo of body weight, administered singly or multiply in doses, e.g. from about 0.01 mg to about 25 mg each. Normally, such a dosage is given orally but parenteral administration may also be chosen.

In the preparation of pharmaceutical formulations containing a compound of the present invention in the form of dosage units for oral administration the compound selected may be mixed with solid, powdered ingredients, such as lactose, saccharose, sorbitol, mannitol, starch, amylopectin, cellulose derivatives, gelatin, or another suitable ingredient, as well as with disintegrating agents and lubricating agents such as magnesium stearate, calcium stearate, sodium stearyl fumarate and polyethylene glycol waxes. The mixture is then processed into granules or pressed into tablets.

Soft gelatine capsules may be prepared with capsules containing a mixture of the active compound or compounds of the invention, vegetable oil, fat, or other suitable vehicle for soft gelatine capsules. Hard gelatine capsules may contain granules of the active compound. Hard gelatine capsules may also contain the active compound in combination with solid powdered ingredients such as lactose, saccharose, sorbitol, mannitol, potato starch, corn starch, amylopectin, cellulose derivatives or gelatine.

Dosage units for rectal administration may be prepared (i) in the form of suppositories which contain the active substance mixed with a neutral fat base; (ii) in the form of a gelatine rectal capsule which contains the active substance in a mixture with a vegetable oil, paraffin oil or other suitable vehicle for gelatine rectal capsules; (iii) in the form of a ready-made micro enema; or (iv) in the form of a dry micro enema formulation to be reconstituted in a suitable solvent just prior to administration.

Liquid preparations for oral administration may be prepared in the form of syrups or suspensions, e.g. solutions or suspensions containing from 0.2% to 20% by weight of the active ingredient and the remainder consisting of sugar or sugar alcohols and a mixture of ethanol, water, glycerol, propylene glycol and polyethylene glycol. If desired, such liquid preparations may contain colouring agents, flavouring agents, saccharine and carboxymethyl cellulose or other thickening agent. Liquid preparations for oral administration may also be prepared in the form of a dry powder to be reconstituted with a suitable solvent prior to use.

Solutions for parenteral, e.g. intravenous, administration may be prepared as a solution of a compound of the invention in a pharmaceutically acceptable solvent, preferably in a concentration from 0.1% to 10% by weight. These solutions may also contain stabilizing ingredients and/or buffering ingredients and are dispensed into unit doses in the form of ampoules or vials. Solutions for parenteral administration may also be prepared as a dry preparation to be reconstituted with a suitable solvent extemporaneously before use. The compounds of the present invention may also be used or administered in combination with one or more additional therapeutically active agents. The components may be in the same formulation or in separate formulations for administration simultaneously or sequentially.

Accordingly, in a further aspect of the invention, there is provided a combination product comprising:
(A) a compound of the invention, as defined herein; and
(B) another therapeutic agent; whereby (A) and (B) is formulated in admixture with a pharmaceutically acceptable excipient.

Such combination products provide for the administration of a compound of the invention in conjunction with the other therapeutic agent, and may thus be presented either as separate formulations, wherein at least one of those formulations comprises a compound of the invention, and at least one comprises the other therapeutic agent, or may be presented (i.e. formulated) as a combined preparation (i.e. presented as a single formulation including a compound of the invention and the other therapeutic agent).

Thus, there is further provided:
(1) a pharmaceutical formulation including a compound of the invention, as hereinbefore defined, another therapeutic agent, and a pharmaceutically acceptable excipient, e.g. an adjuvant, diluent or carrier; or
(2) a kit of parts comprising, as components:
(a) a pharmaceutical formulation including a compound of the invention, as defined herein, in admixture with a pharmaceutically acceptable excipient, e.g. an adjuvant, diluent or carrier; and
(b) a pharmaceutical formulation including another therapeutic agent in admixture with a pharmaceutically acceptable excipient, e.g. an adjuvant, diluent or carrier, which components (a) and (b) are each provided in a form that is suitable for administration in conjunction with the other.

In some particular embodiments, the compound of the invention is used in a combination with an antitumor agent in the treatment of a malignant hyperproliferative disease. Such combination therapy may be particularly useful in cancer chemotherapy, to counteract an anti-apoptotic effect of Nox4 that may lead to tumor resistance to the antitumor agent.

Thus, there is further provided:
(1) a pharmaceutical formulation including a compound of the invention, as hereinbefore defined, an antitumor agent, and a pharmaceutically acceptable excipient, e.g. an adjuvant, diluent or carrier; or
(2) a kit of parts comprising, as components:
(a) a pharmaceutical formulation including a compound of the invention, as defined herein, in admixture with a pharmaceutically acceptable excipient, e.g. an adjuvant, diluent or carrier; and
(b) a pharmaceutical formulation including an antitumor agent in admixture with a pharmaceutically acceptable excipient, e.g. an adjuvant, diluent or carrier, which components (a) and (b) are each provided in a form that is suitable for administration in conjunction with the other.

The components (a) and (b) in any of the above kit of parts may be administered at the same time, in sequence, or separately from each other.

The compounds of the present invention may also be used or administered in combination with other modes of treatment such as irradiation for the treatment of cancer.

According to one aspect, there is provided a method of inhibiting the activity of Nox, in particular Nox4, in a patient in need thereof, by administering to said patient a therapeutically effective amount of a compound of formula (I) as defined herein. The patient may be any mammal, but preferably is a human.

The patient to be treated may be one suffering from a condition or disorder associated with an elevated activity of Nox, in particular Nox4, or a patient at risk of developing such a condition or disorder. Examples of such conditions and disorders are cardiovascular disorders, respiratory disorders, metabolism disorders, skin disorders, bone disorders, neuroinflammatory and/or neurodegenerative disorders, kidney diseases, reproduction disorders, diseases affecting the eye and/or the lens and/or conditions affecting the inner ear, inflammatory disorders, liver diseases, pain, cancers, allergic disorders, traumatisms, septic, hemorrhagic and anaphylactic shock, diseases or disorders of the gastrointestinal system, angiogenesis, angiogenesis-dependent conditions, lung infections, acute lung injury, pulmonary arterial hypertension, obstructive lung disorders, fibrotic lung disease, and lung cancer.

In one embodiment, the compounds of the present invention are for use in the treatment of stroke. In one particular embodiment, the stroke is ischemic. The compounds of the present invention are considered to have neuroprotective activity in the treatment of stroke. Therefore, the compounds of the present invention suitable are used in combination with removal of blood clots in the treatment of ischemic stroke. In one particular embodiment, the compounds of the present invention are used in combination with tPA in the treatment of ischemic stroke.

The invention will be illustrated by the following, non-limiting Examples.

EXAMPLES

Example 1

Cell-Based Assays and Analytical Chemistry

1. Cell Viability
   1.1 Celltiter-Blue Cell Viability Assay (Promega)

The assay is based on the ability of the cells to reduce resazurin to resorufin as a measure of viability. TREx™-293 Nox4 cells were cultured in a T-225 flask, collected by trypsination and re-suspended in cell medium. 20,000 cells in 90 µl were seeded to 96-well cell culture plates (black with transparent bottom). One background plate with 90 µl cell medium only was also prepared.

After 24 hours, 10 µl of compound, diluted to 10 times final concentration in 37° C. cell medium, were added to cell and background plates. The compounds were tested in duplicate at a final concentration of 10 µM. Chlorpromazine, at a final concentration of 100 µM, was added as positive control. After 24 hours of treatment, 20 µl of CellTiter-Blue reagent were added and the plate was incubated for 120 min at 37° C. Resorufin fluorescence was read in Victor2V plate reader. All experimental values were corrected for background before analysis of the cell viability.

1.2 CytoTox 96® Non-Radioactive Cytotoxicity Assay (Promega)

The assay is based on lactate dehydrogenase (LDH) activity in surrounding cell medium as a measure of membrane integrity. Membrane integrity can be affected by apoptosis, necrosis or chemicals. TREx™-293 Nox4 cells were cultured in a T-225 flask, collected by trypsination and re-suspended in HBSS to 100,000 cells per ml. 90 µl of cell suspension were added to each well of a V-bottom polypropylene 96-well plate. One background plate was prepared with HBSS only. Compounds were diluted in HBSS to 10 times final concentration and 10 µl was added per well. The compounds were tested in duplicate at a final concentration of 10 µM.

Plates were incubated 3 hours at 37° C. 45 minutes before end of incubation time, 10 µl of lysis solution (Triton X-100) were added to total control wells to estimate total LDH content of cells. Spontaneous LDH leakage was determined with un-treated cells.

Cell plates were centrifuged 250×g for 5 minutes and 50 µl of supernatant were transferred to 96-well Spectraplates. 50 µl of reconstituted substrate mix were added and plates were incubated for 30 minutes at room temperature. 50 µl of stop solution were added and plates were read in SpectraMax® at a wavelength of 490 nm. Compound specific background was subtracted and % cytotoxcity was calculated as:

[(Experimental−Spontaneous)/(Total−Spontaneous)]*100%.

When tested in the two cell viability assays, none of the inventive compounds showed any significant cell toxicity effects.

2. Dose-Response Curves

Dose-response measurements with the Amplex® Red based assay were performed as follows: Compound serial dilution was carried out using the system based on the liquid handler Janus® (Perkin Elmer) and scheduling software Overlord (Process Analysis and Automation).

Starting with compound plates with 15 µl 10 mM compound stock solution in DMSO, 10 µl of DMSO were added to columns of compound plate (Flexdrop). Serial dilution was performed by adding 5 µl compound solution to 10 µl DMSO (1:3) to 11 concentrations. To each well of the compound plate 90 µl of assay buffer were added. After mixing, 10 µl were transferred from each well of the compound plate to wells of an assay plate, followed by addition of 20 µl detection mix and 20 µl of a suspension of TREx™-293 Nox4 cells. The assay plate then was incubated for 40-60 min at room temperature.

Data was analyzed using a custom calculation template in Activitybase XE (IDBS). Raw fluorescence data was transformed to % inhibition using the built-in formula:

$$\% \text{ inhibition} = 100 - \frac{RawData_{Compound} - RawData_{Low}}{RawData_{High} - RawData_{Low}} \times 100$$

Dose-response curves were fitted using non-linear regression with four parameter logistic formula. FIGS. 1A-E show dose-response curves for some compounds of the invention. The tested compounds have 1050 values ranging from about 1 µM to about 68 µM.

Example 2

In Vivo Study: Stroke Animal Model

Mice (10-12 wk), wild type C57Bl6, 6 animals, were used:

Control (n=3) stroke induced mouse treated i.p. with vehicle 2 h and 12 h.

Test (n=3) stroke induced mouse treated i.p. with inventive compound M4 ($N^2$-(3,4-dimethylphenyl)-6-((4-(3-methoxyphenyl)piperazin-1-yl)methyl)-1,3,5-triazine-2,4-diamine).

M4 preparation for intra peritoneal i.p. administration: 3.5 mg of M4 were first dissolved in 1 ml of DMSO. After the substance was totally dissolved, 5 ml of 20% Cremophor ELP in PBS (phosphate buffered saline solution) was added. Thereafter an additional 4 ml of PBS was added. The 20% Cremophor ELP solution was prepared by dissolving 10.5 g of Cremophor in 50 ml of PBS.

Final concentration of the injection solution: 0.35 mg/ml.

Injection volume of M4: The dose was 3.2 mg/kg, calculated for each animal at each event of administration (2 h and 12 h).

Procedure:
1. Transient middle cerebral artery occlusion (tMCAO) by blocking with a filament for 1 h.
2. Reperfusion after 1 h by removing filament
3. Injection of M4 by i.p. after 2 h and repeated injection i.p. after 12 h
4. Sacrifice the animal after 24 h and infarct size is determined by triphenyl tetrazolium chloride (TTC) staining—Thus the procedure of middle cerebral artery occlusion (MCAO); 1 h occlusion and 23 h reperfusion.
5. Stroke analysis was performed as described previously (Experimental Neurology 200 (2006), pp. 480-485; Circulation May 1, 2007, pp. 2323-2330). To determine infarct size, mice were killed 24 h after tMCAO, pMCAO, or cortical photothrombosis. Brains were cut in 2-mm-thick coronal sections using a mouse brain slice matrix (Harvard Apparatus). The slices were stained with 2% TTC (Sigma-Aldrich) to visualize the infarcts. Planimetric measurements (ImageJ software, United States National Institutes of Health), calculating lesion volumes, were corrected for brain edema as described previously (Ann Neurol 2003; 54:330-342).

Animal Studies

Animal studies were approved by the Regierung von Unterfranken and conducted according to the recently published recommendations for research in mechanism-driven basic stroke studies. Adult male C57/BL6 mice (20 to 25 g) were purchased from Charles River (Sulzfeld, Germany). The tMCAO model was used to induce focal cerebral ischemia as described in detail elsewhere. Briefly, mice were anesthetized with 2% isoflurane in a 70% N2O/30% O2 mixture. A servo-controlled heating blanket was used to maintain core body temperature close to 37° C. throughout surgery. After a midline neck incision was made, a standardized silicon rubber-coated 6.0 nylon monofilament (60-1720RE, Doccol, Redlands, Calif.) was inserted into the right common carotid artery and advanced via the internal carotid artery to occlude the origin of the MCA. After 1 hour, mice were reanesthetized, and the occluding filament was removed to allow reperfusion. All animals were operated on by the same operator to reduce infarct variability; operation time per animal did not exceed 15 minutes.

Determination of Infarct Size

Figure 2:
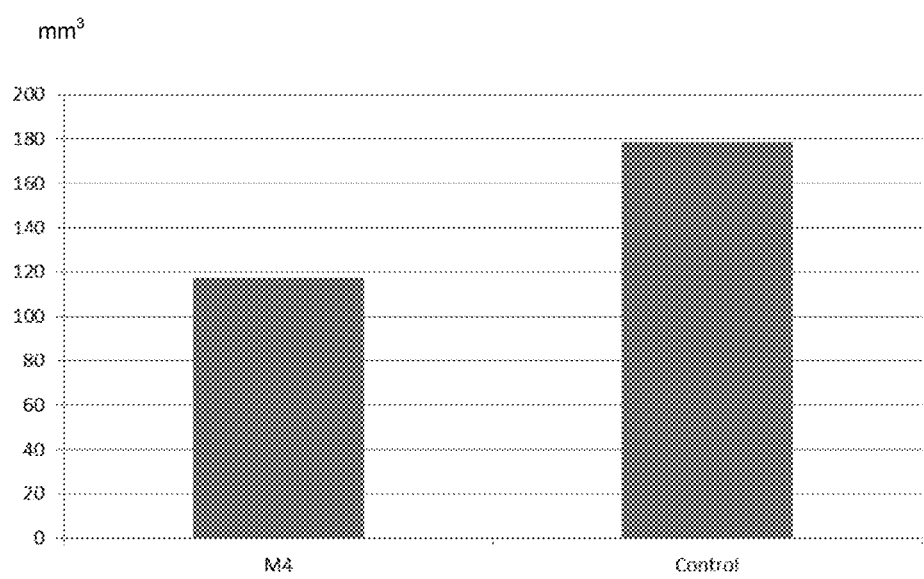
FIG. 2 is a bar chart showing the mean infarct volume, in mm³, in brain from stroke induced mice treated by i.p. injection of N²-(3,4-dimethylphenyl)-6-((4-(3-methoxyphenyl)piperazin-1-yl)methyl)-1,3,5-triazine-2,4-diamine (M4) or of vehicle (Control), respectively.

Mice were killed 24 hours after tMCAO. Brains were quickly removed and cut into 2-mm-thick coronal sections using a mouse brain slice matrix. The slices were stained with 2% 2,3,5-triphenyltetrazolium chloride (TTC; Sigma-Aldrich, Seelze, Germany) in PBS to visualize the infarctions. Planimetric measurements (ImageJ software, National Institutes of Health, Bethesda, Md.) were performed by researchers blinded to the treatment group and were used to calculate lesion volumes, which were corrected for brain edema as described elsewhere. The occurrence of Intra Cerebral Hemorrhage (ICH) was macroscopically assessed on whole brains and again after the 2-mm-thick coronal brain slices were cut (see above) before TTC staining. Brains showing ICH were excluded from the assessment of infarct volume. The results for the tree mice treated with M4 and the three control mice, respectively, are shown in Table 2. FIG. 2 is a bar chart showing the mean infarct volume for the group treated with M4 and the control group, respectively.

TABLE 2

| Infarct volume, mm³ | |
| --- | --- |
| Animals treated with M4 | Control animals |
| 73 | 107 |
| 145 | 224 |
| 134 | 204 |

The invention claimed is:

1. A method of inhibiting NOX4 in a mammal, wherein the inhibition of NOX4 is used to treat a disorder or condition selected from the group consisting of endocrine disorders, cardiovascular disorders, respiratory disorders, metabolism disorders, skin disorders, bone disorders, neuroinflammatory and/or neurodegenerative disorders, kidney diseases, reproduction disorders, diseases affecting the eye and/or the lens and/or conditions affecting the inner ear, inflammatory disorders, liver diseases, pain, cancers, lung cancer, allergic disorders, traumatisms, septic, hemorrhagic and anaphylactic shock, diseases or disorders of the gastrointestinal system, angiogenesis, angiogenesis-dependent conditions, lung infections, acute lung injury, pulmonary arterial hypertension, obstructive lung disorders, and fibrotic lung disease, the method comprising administering, to a mammal in need thereof, a compound of formula (I)

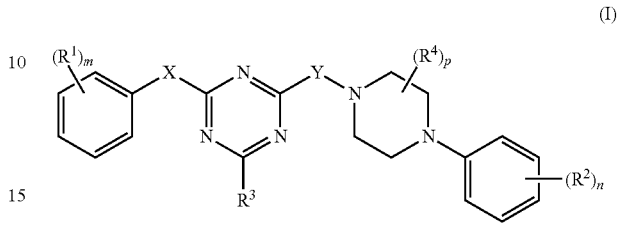

wherein each $R^1$, $R^2$ and $R^3$ is independently selected from halogen, $R^5O(CH_2)_q$, $R^5S(CH_2)_q$, $R^6R^7N(CH_2)_q$, $CN(CH_2)_q$, C1-C6 alkyl, C2-C6 alkenyl, C2-C6 alkynyl, and C3-C6 cycloalkyl, said alkyl, alkenyl, alkynyl and cycloalkyl optionally being substituted with at least one halogen;

each $R^4$ is independently selected from halogen, C1-C6 alkyl, C2-C6 alkenyl, C2-C6 alkynyl, and C3-C6 cycloalkyl, said alkyl, alkenyl, alkynyl and cycloalkyl optionally being substituted with at least one halogen;

each $R^5$ is independently selected from H, C1-C6 alkyl, C2-C6 alkenyl, C2-C6 alkynyl, and C3-C6 cycloalkyl, said alkyl, alkenyl, alkynyl and cycloalkyl optionally being substituted with at least one halogen;

each $R^6$ and $R^7$ is independently selected from H, C1-C6 alkyl, C2-C6 alkenyl, C2-C6 alkynyl, and C3-C6 cycloalkyl, said alkyl, alkenyl, alkynyl and cycloalkyl optionally being substituted with at least one halogen;

X is NH, $CH_2$ or C(O);

Y is NH; $CH_2$ or C(O);

m is an integer of from 0 to 5;

n is an integer of from 0 to 5;

p is an integer of from 0 to 4; and q is an integer of from 0 to 3;

or a pharmaceutically acceptable salt thereof.

2. The method according to claim 1, wherein each $R^1$ is independently selected from halogen, C1-C6 alkyl, C2-C6 alkenyl, C2-C6 alkynyl, and C3-C6 cycloalkyl, said alkyl, alkenyl, alkynyl and cycloalkyl optionally being substituted with at least one halogen.

3. The method according to claim 1, wherein each $R^2$ is independently selected from halogen, $R^5O(CH_2)_q$, and $R^5S(CH_2)_q$.

4. The method according to claim 2, wherein each $R^2$ is independently selected from halogen, $R^5O(CH_2)_q$, and $R^5S(CH_2)_q$.

5. The method according to claim 1, wherein $R^3$ is $R^6R^7N(CH_2)_q$.

6. The method according to claim 2, wherein $R^3$ is $R^6R^7N(CH_2)_q$.

7. The method according to claim 3, wherein $R^3$ is $R^6R^7N(CH_2)_q$.

8. The method according to claim 4, wherein $R^3$ is $R^6R^7N(CH_2)_q$.

9. The method according to claim 1, wherein both $R^6$ and $R^7$ are H.

10. The method according to claim 5, wherein both $R^6$ and $R^7$ are H.

11. The method according to claim 1, wherein m is an integer of from 0 to 2.

12. The method according to claim 1, wherein n is 0 or 1.

13. The method according to claim 1, wherein p is 0.

14. The method according to claim 1, wherein X is NH.

15. The method according to claim 1, wherein Y is $CH_2$.

16. The method according to claim 14, wherein Y is $CH_2$.

17. The method according to claim 1, wherein each $R^1$ is independently selected from halogen and C1-C6 alkyl, said alkyl optionally being substituted with at least one halogen;

each $R^2$ is independently selected from halogen and $R^5O$;

$R^3$ is $NH_2$;

$R^5$ is C1-C6 alkyl;

X is NH;

Y is $CH_2$;

m is an integer of from 0 to 2;

n is 0 or 1; and p is 0.

18. The method according to claim 1, wherein the compound of formula (I) is selected from $N^2$-(3,4-dimethylphenyl)-6-((4-(3-methoxyphenyl)piperazin-1-yl)methyl)-1,3,5-triazine-2,4-diamine;

$N^2$-(3-chloro-4-methylphenyl)-6-((4-(3-methoxyphenyl)piperazin-1-yl)methyl)-1,3,5-triazine-2,4-diamine;

6-((4-phenylpiperazin-1-yl)methyl)-$N^2$-(p-tolyl)-1,3,5-triazine-2,4-diamine;

$N^2$-phenyl-6-((4-phenylpiperazin-1-yl)methyl)-1,3,5-triazine-2,4-diamine; and 6-((4-(4-fluorophenyl)piperazin-1-yl)methyl)-$N^2$-phenyl-1,3,5-triazine-2,4-diamine;

or a pharmaceutically acceptable salt thereof.

19. The method according to claim 1, wherein the disorder or condition is selected from diabetes, stroke and lung fibrosis.

20. A pharmaceutical composition comprising a compound selected from $N^2$-(3,4-dimethylphenyl)-6-((4-(3-methoxyphenyl)piperazin-1-yl)methyl)-1,3,5-triazine-2,4-diamine;

$N^2$-(3-chloro-4-methylphenyl)-6-((4-(3-methoxyphenyl)piperazin-1-yl)methyl)-1,3,5-triazine-2,4-diamine;

6-((4-phenylpiperazin-1-yl)methyl)-$N^2$-(p-tolyl)-1,3,5-triazine-2,4-diamine;

$N^2$-phenyl-6-((4-phenylpiperazin-1-yl)methyl)-1,3,5-triazine-2,4-diamine; and 6-((4-(4-fluorophenyl)piperazin-1-yl)methyl)-$N^2$-phenyl-1,3,5-triazine-2,4-diamine;

or a pharmaceutically acceptable salt thereof, and optionally at least one pharmaceutically acceptable excipient.

21. The method according to claim 1, wherein the disorder or condition is diabetes.

22. The method according to claim 1, wherein the disorder or condition is stroke.

23. The method according to claim 1, wherein the disorder or condition is lung fibrosis.

* * * * *